(12) United States Patent
Wilkins

(10) Patent No.: US 8,012,123 B2
(45) Date of Patent: Sep. 6, 2011

(54) CATHETER WITH GUIDEWIRE LUMEN WITH TUBULAR PORTION AND SLEEVE

(75) Inventor: Douglas P. Wilkins, San Jose, CA (US)

(73) Assignee: Taylor Medical, Inc., Campbell, CA (US)

(*) Notice: Subject to any disclaimer, the term of this patent is extended or adjusted under 35 U.S.C. 154(b) by 116 days.

(21) Appl. No.: 11/970,677

(22) Filed: Jan. 8, 2008

(65) Prior Publication Data

US 2008/0177227 A1    Jul. 24, 2008

Related U.S. Application Data

(60) Provisional application No. 60/886,009, filed on Jan. 22, 2007.

(51) Int. Cl.
*A61M 29/00*    (2006.01)

(52) U.S. Cl. ........................................ 604/103

(58) Field of Classification Search ........... 604/103, 604/524, 526
See application file for complete search history.

(56) References Cited

U.S. PATENT DOCUMENTS

| | | | |
|---|---|---|---|
| 4,702,252 A * | 10/1987 | Brooks et al. ............... | 606/195 |
| 4,898,591 A * | 2/1990 | Jang et al. .................. | 604/527 |
| 5,078,727 A * | 1/1992 | Hannam et al. ............. | 606/194 |
| 5,304,134 A * | 4/1994 | Kraus et al. ................. | 604/96.01 |
| 5,378,237 A * | 1/1995 | Boussignac et al. ........ | 604/103.01 |
| 5,383,853 A * | 1/1995 | Jung et al. ................... | 604/103.04 |
| 5,797,877 A * | 8/1998 | Hamilton et al. ........... | 604/96.01 |
| 5,820,594 A * | 10/1998 | Fontirroche et al. ........ | 604/165.01 |
| 5,824,173 A * | 10/1998 | Fontirroche et al. ........ | 156/86 |
| 6,165,166 A * | 12/2000 | Samuelson et al. .......... | 604/524 |
| 6,500,147 B2 * | 12/2002 | Omaleki et al. ............ | 604/103.09 |
| 6,958,059 B2 * | 10/2005 | Zadno-Azizi ................ | 604/509 |
| 7,485,108 B2 * | 2/2009 | Kastenhofer ................ | 604/96.01 |
| 2002/0082549 A1 * | 6/2002 | Duchamp ..................... | 604/96.01 |
| 2002/0177800 A1 * | 11/2002 | Bagaoisan et al. .......... | 604/6.12 |
| 2003/0088153 A1 * | 5/2003 | Carrillo et al. ............. | 600/114 |
| 2004/0199240 A1 * | 10/2004 | Dorn ........................... | 623/1.11 |

FOREIGN PATENT DOCUMENTS

EP    0650740 A1    5/1995

OTHER PUBLICATIONS

International Search Report for corresponding International Application PCT/US2008/050464.
International Preliminary Report on Patentability for corresponding International Application PCT/US2008/050464.

* cited by examiner

*Primary Examiner* — Nicholas D Lucchesi
*Assistant Examiner* — Diva Ranade
(74) *Attorney, Agent, or Firm* — WRB-IP LLP

(57) ABSTRACT

A guidewire lumen for a catheter includes a tubular portion and a sleeve bonded over less than an entire length of the tubular portion. The tubular portion is formed of a first material and the sleeve is formed of a second material. The second material may bond better to certain materials than the first material.

37 Claims, 3 Drawing Sheets

CATHETER WITH GUIDEWIRE LUMEN WITH TUBULAR PORTION AND SLEEVE

BACKGROUND AND SUMMARY

The present invention relates to catheters and catheter components and, more particularly, to catheters and catheter components including guidewire lumens with sleeves.

Catheters used to treat, e.g., blocked arteries in coronary, peripheral, and neurovascular fields are typically guided to a treatment site by riding over a guidewire. Although the guidewire is sometimes coated with a friction-reducing material such as TEFLON, there is generally some friction when a plastic catheter is pushed over the wire.

In the past, in balloon catheters, polyethylene was used as the balloon material in the catheter. This allowed the use of low friction, High Density Polyethylene (HDPE) as the lumen for the guidewire. A low profile heat bond could be performed at the distal tip of the balloon and the guidewire lumen to allow for a smooth transition and a soft tip.

As more advanced and stronger materials have been developed for the balloon, such as Polyester (PET), Nylon, and Acrylon (Acrylonitrile), a need for an alternative to HDPE has arisen. HDPE as a single material cannot be heat bonded to materials such as Polyester, Nylon, and Acrylon. Some of the materials that can be bonded to Nylon balloons include Polyether Block Amide (PEBAX) and Nylon, however, these materials tend to have higher surface friction than HDPE. One solution has been to coextrude an inner layer of HDPE or TEFLON and an outer layer of some other material, such as PEBAX. This is more costly than an HDPE extrusion, and the coextrusion can result in delamination. Alternatively, an adhesive bond has been used. However, adhesive bonds tend to be undesirably stiff and have a relatively high profile.

Materials with low surface friction such as HDPE, and various fluoropolymers such as PolyTetraFluoroEthylene (PTFE) (also known as TEFLON as manufactured by DuPont), TetraFluorEthylene-Perfluorpropylene (FEP), and PerFluoroAlkoxy (PFA), cannot be heat bonded to many modern balloon materials and are difficult to process. Materials presently used as the guidewire lumen for Nylon balloons are commonly Polyether Block Amide (PEBAX), Nylon 11, Nylon 12, or blends of these materials. Materials used for PET and Acrylon balloons are Hytrel and PET/Polyurethane blends. Polyurethane balloons used for neuro applications also commonly use polyurethane or PEBAX inner wire lumens. All of these materials have high surface frictions at body temperature and have the potential to interfere with guidewire movement.

It is desirable to provide a material suitable for use in a catheter having a low surface friction and that is flexible and easy to process. It is particularly desirable to provide such a material for use in connection with a guidewire lumen.

In accordance with an aspect of the present invention, a guidewire lumen for a catheter comprises a tubular portion and a sleeve disposed over less than an entire length of the tubular portion, the tubular portion being formed of a first polymer and the sleeve being formed of a second polymer, the second polymer comprising one or more of a polyamide, a nylon, a polyether block amide, and polyurethane.

In accordance with another aspect of the present invention, a guidewire lumen for a catheter comprises a tubular portion formed of a first material and a sleeve formed of a second material disposed around part of the tubular portion, and a metallic marker band disposed around a portion of the tubular portion, the sleeve being disposed over the marker band and extending from proximate a distal end of the tubular portion to a point proximal of and proximate the marker band.

In accordance with another aspect of the present invention, a method of making a catheter comprises providing a sleeve over less than an entire length of a tubular portion of a guidewire lumen, the tubular portion being formed of a first material and the sleeve being formed of a second material, providing a marker band over the tubular portion and beneath the sleeve, and bonding the sleeve to a catheter component.

In accordance with another aspect of the present invention, a catheter comprises a guidewire lumen comprising a tubular portion and proximal and distal sleeves disposed over less than an entire length of the tubular portion, the tubular portion being formed of a first material and the sleeves being formed of a second material, and a metallic marker band disposed between the distal sleeve and the tubular portion, a balloon bonded to the distal sleeve, and a catheter shaft bonded to the proximal sleeve.

BRIEF DESCRIPTION OF THE DRAWINGS

The features and advantages of the present invention are well understood by reading the following detailed description in conjunction with the drawings in which like numerals indicate similar elements and in which.

DETAILED DESCRIPTION

Figure 1:
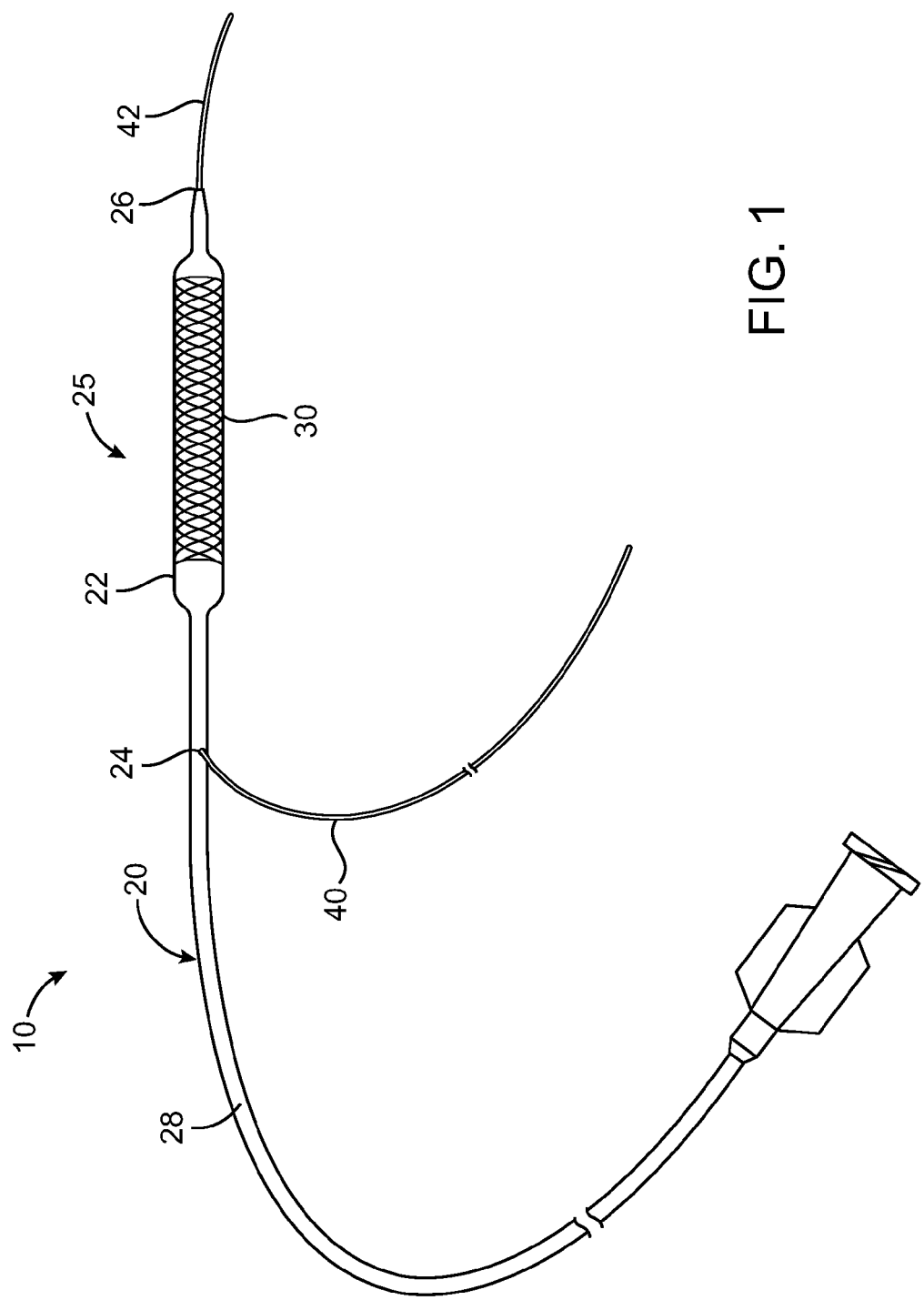
FIG. 1 is a side perspective view of a catheter system.
Figure 2:
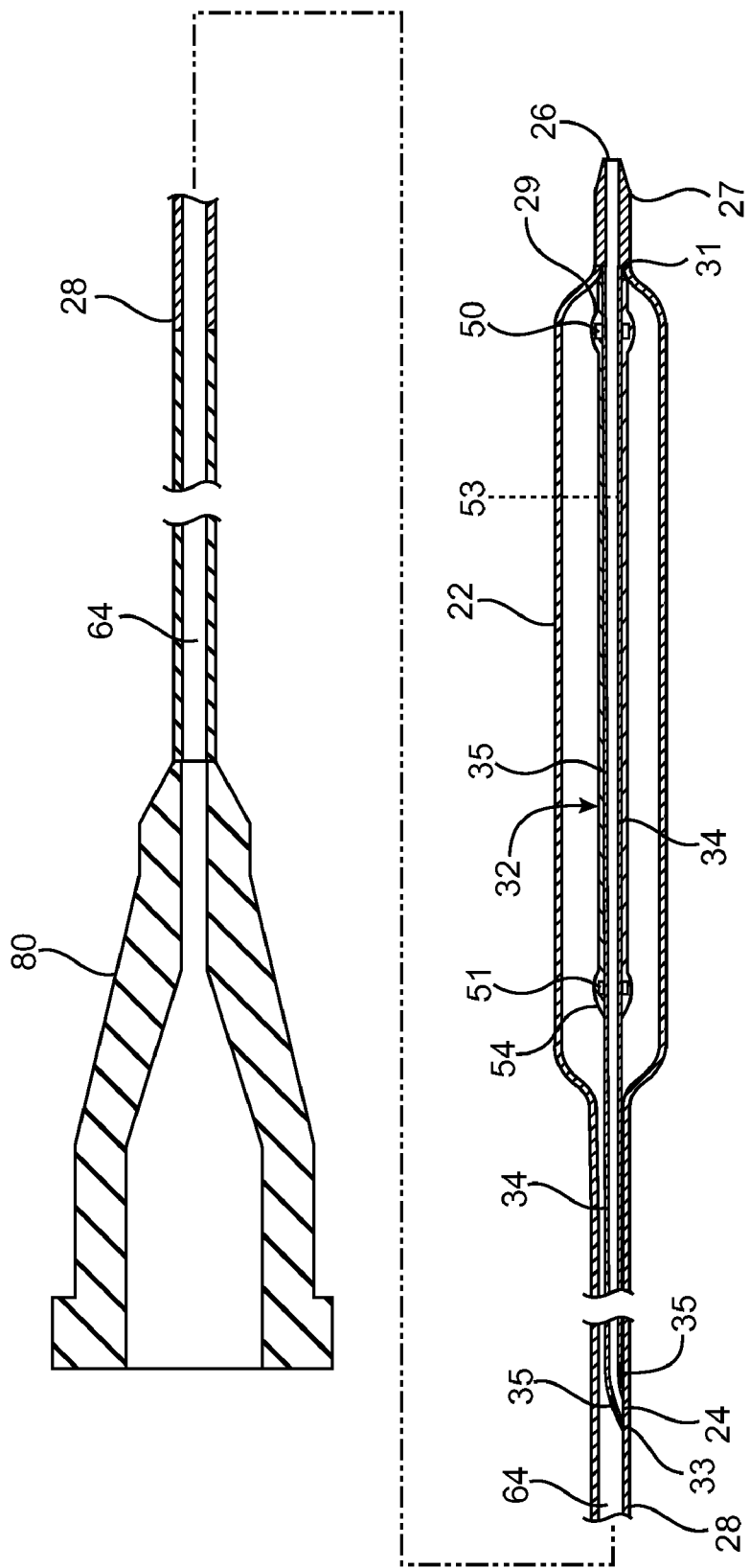
FIG. 2 illustrates a side, elevational, longitudinal cross-sectional view, with central portions broken away, of the catheter illustrated in FIG. 1.

A catheter system 10 comprises a catheter 20 according to an embodiment of the present invention and is shown in FIGS. 1 and 2. The catheter 20 can be a conventional catheter, such as an over-the-wire type catheter or, as shown, a rapid exchange type catheter. The catheter 20 comprises a guidewire lumen 32 through which a guidewire can extend. A proximal portion 40 of the guidewire can extend out of the catheter through a proximal guidewire port 24, or rapid exchange or RX port, that is proximal of a balloon 22, and a distal portion 42 of the guidewire can extend out of a distal guidewire port 26 distal of the balloon 22. The guidewire lumen 32 comprises a tubular portion 34 (also referred to as a guidewire lumen or inner member) having an inner opening through which the guidewire 40 can extend. A catheter shaft 28 extends between a hub structure 80 at or proximate a proximal end of the catheter shaft and the balloon 22 at or proximate a distal end of the shaft. The catheter shaft 28 defines an inflation lumen 64. The balloon 22 may be used for angioplasty to expand a stent 30 or for other purposes.

A diameter of the guidewire lumen 32 varies from an outside diameter of about 0.013-0.040 inches (0.33-1.02 mm), and an inside diameter of about 0.010-0.035 inches (0.25-0.89 mm), depending upon the type of catheter. In coronary catheters, the guidewire lumen 32 ordinarily has an outside diameter of about 0.019-0.022 inches (0.48-0.56 mm), and an inside diameter of about 0016-0.018 inches (0.41-0.46 mm). For neurocatheters, the outside diameter is typically about 0.013-0.015 inches (0.33-0.38 mm) and the inside diameter is typically about 0.010-0.012 inches (0.25-0.30 mm). In peripheral vascular catheters, an inside diameter is typically about 0.018-0.021 inches (0.46-0.53 mm) and an outside diameter is typically about 0.023-0.026 inches (0.58-

0.66 mm). In biliary catheters, an inside diameter is typically about 0.033-0.036 inches (0.84-0.91 mm) and an outside diameter is typically about 0.036-0.039 inches (0.91-0.99 mm).

At least a portion of the tubular portion 34 of the guidewire lumen 32, generally substantially the entire tubular portion, is formed of a material having a low coefficient of friction, such as High Density Polyethylene (HDPE). A sleeve 35 is disposed around less than an entire length of the tubular portion 34. The sleeve 35 can be bonded to the tubular portion 34, such as by bonding with heat and pressure, or with an adhesive, or both. The sleeve 35 will ordinarily be formed of a polymer material that bonds well, at least compared to HDPE, to the material, e.g., PET, Nylon, and Acrylonitrile, from which the balloon 22 is formed. The sleeve 35 can, for example, be formed from a polymer material such as PEBAX.

The polymer of the sleeve 35 ordinarily comprises one or more of a polyamide, a nylon, a PEBAX, and polyurethane. The material for the sleeve 35 for coronary catheters is typically PEBAX 72D or 70D or materials of similar hardness. Larger catheters can use these inner lumen materials or stiffer materials for the sleeve 35. For neuro applications, the material for the sleeve 35 is typically a softer material such as PEBAX 70D, 63D or 55D.

The polymer forming the tubular portion 34 of the guidewire lumen 32 typically has lower friction passing over a conventional guidewire than the friction between the same guidewire passing over the polymer forming the sleeve 35. The tubular portion 34 and the sleeve 35 of the guidewire lumen 32 can each be extruded as single integral layers and thereafter bonded together by suitable means, such as with heat and pressure, with adhesive, or both, however, they can alternatively be coextruded. When forming part of the catheter 20, a catheter component such as a distal end 29 of a balloon 22 and/or a catheter shaft 28 of the catheter at the proximal guidewire port 24 can be bonded to the sleeve 35 of the guidewire lumen 32 by any suitable technique, such as by application of heat and pressure, radio frequency bonding, and/or laser bonding. The bond will ordinarily be formed without use of an adhesive, which tends to make a stiff bond having a high profile.

Figure 3:
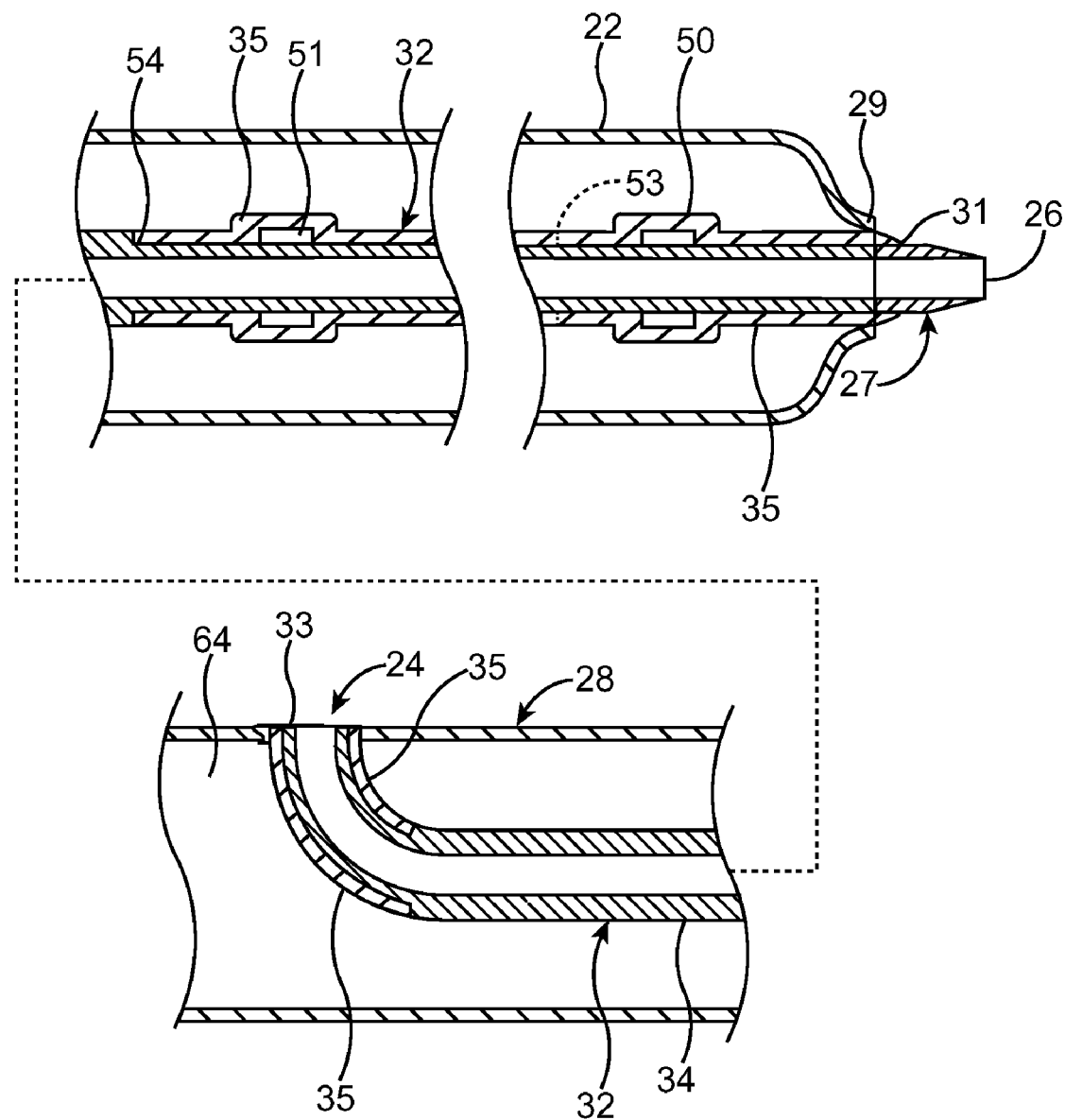
FIG. 3 illustrates a side, elevational, longitudinal cross-sectional view, with central portions broken away, of a portion of the catheter illustrated in FIG. 2.

The catheter 20 can include a tip 27 disposed at a distal end 31 of the guidewire lumen 32. The tip 27 may be integrally formed with the tubular portion 34 or, as illustrated in FIG. 3, can be bonded to an end of the tubular portion. The tip 27 may be formed of the same or a different material than the tubular portion 34. The sleeve 35 may extend partially over a proximal end of the tip 27 and facilitate bonding the tip to the tubular portion 34, either by itself or in conjunction with other means of bonding, such as adhesive, application of heat and pressure, radio frequency bonding, and/or laser bonding.

A distal marker 50 can be bonded around the tubular portion 34 proximate a distal end of the tubular portion to facilitate locating the tubular portion and a distal end 29 of the balloon 22 in a patient's body. A proximal marker 51 can also be bonded around the tubular portion 34 proximate a proximal end of the balloon 22 to facilitate locating the tubular portion and the proximal end of the balloon in the patient's body. The distal marker 50 and the proximal marker 51 will ordinarily be formed of a metallic material. The sleeve 35 will ordinarily extend from at least a distal end 52 of the tubular portion 34 to a point 53 (shown in phantom in FIG. 3) proximal of the distal marker 50 or to a point 54 proximal of the proximal marker 51.

By providing the sleeve 35 over the markers 50 and 51, the potential for pinholing the balloon 22 can be reduced when a stent 30 is crimped at high pressures over the balloon 22 because the sleeve can present softer edges and preventing pinching of the balloon material between the metallic stent and the markers. Whether the sleeve 35 extends to a point proximal the proximal marker 51 or only to a point proximal the distal marker 50 largely depends upon whether additional protection against pinholing and the like is desired, in addition to improving the bondability of the tubular portion 34 to the balloon 22.

In addition, providing the markers 50 and 51 between the tubular portion 34 and the sleeve 35 can improve the bond between the tubular portion 34 and the sleeve 35, particularly when the bond, i.e., the bond strength per unit area, between the markers and the tubular portion and the bond between the markers and the sleeve is stronger than the bond between the tubular portion and the sleeve.

The tubular portion 34 may have a constant diameter over its entire length. Alternatively, as shown in FIG. 3, the tubular portion 34 may have a reduced diameter proximate the sleeve 35 at the proximal end 33 of the guidewire lumen 32 that is bonded to the catheter shaft 28 to form the proximal guidewire port 24 and/or a reduced diameter proximate the sleeve at the distal end 31 of the guidewire lumen that is bonded to the distal end 29 of the balloon 22. This may be achieved by, for example, necking the proximal and distal ends of the tubular portion 34 before adding the sleeves 35. The guidewire lumen 32 may have a variety of configurations. It will ordinarily have a constant inner diameter to fit the guidewire, but the outer diameter of the guidewire lumen may vary. For example, the outer diameter of the guidewire lumen may have a constant diameter over its entire length, it may have a greater diameter where the sleeve 35 and/or the markers 50 and 51 are provided, or may, as shown in FIG. 3, have a constant diameter over substantially all of the length of the guidewire lumen except where the markers 50 and 51 are provided. As a practical matter, although FIGS. 2 and 3 show an enlarged diameter of the guidewire lumen 32 where the sleeve 35 is bonded over the markers 50 and/or 51, during bonding the polymer of the sleeve will ordinarily tend to become thinner and wall thickness of the guidewire lumen including the tubular portion 34, the sleeve(s), and the markers, if provided, will be substantially uniform.

In a currently contemplated aspect of the present invention, the balloon 22 is typically about 10 mm-40 mm in length. The sleeve 35 will typically be about 10 mm in length, or less, and is typically provided at least one of, typically both, of a proximal end of the tube 34 and at a distal end of the tube.

The bond strength may be measured in any suitable fashion. One technique for measuring the bond strength of a bond between the distal end 29 of the balloon 22 and the sleeve 35 of the guidewire lumen 32 essentially involves separating the bonded part of the balloon and the sleeve from the rest of the catheter, turning the balloon inside out, and pulling on the balloon and guidewire lumen. Bond strength between the catheter shaft 28 and the sleeve 35 of the guidewire lumen 32, such as occurs at the "rapid-exchange" (RX) opening, i.e., proximal guidewire port 24, of the catheter shaft is also important and can be measured by, for example, pulling the catheter shaft and the guidewire lumen apart.

In a method of making a catheter 20, the sleeve 35 can be bonded over less than an entire length of the tubular portion 34 of the guidewire lumen 32. The tubular portion 34 can be formed of a first material and the sleeve 35 can be formed of a second material that is different than the first material. Markers 50 and 51 may be bonded between the sleeve 35 and the tubular portion 34. The sleeve 35 can be bonded to a catheter component such as a balloon 22 that is bonded around the sleeve and/or to a catheter shaft 28 that is bonded around the sleeve. The sleeve 35 can be bonded to the tubular portion 34 by heat and pressure, by an adhesive, or both, or the sleeve can be coextruded with the tubular portion over portions of the tubular portion.

If it is desired to reduce friction between a guidewire and a tubular portion 34 of a guidewire lumen 32, a compound for the tubular portion can formed comprising a polymer and between 2-15% particles or fibers. The compound can be formed by, for example, compounding or mixing in a double screw extruder. The tubular portion 34 can be formed from the compound as a tubular extrusion. The tubular extrusion forms at least a portion of the guidewire lumen 32, a sleeve 35 formed of a material that may have greater friction with a guidewire can be bonded around the tubular portion 34 to facilitate bonding of the guidewire lumen to a catheter component such as by having a distal end of the guidewire lumen bonded to a distal end 29 of a balloon 22. Alternatively, or in addition, the catheter component to which the guidewire lumen 32 might be bonded can comprise a catheter shaft 28.

Although the material described herein is described with respect to an inner tubular portion 34 of the guidewire lumen 32 member for a rapid exchange or over the wire catheter, the reduced friction and good bondability by providing the stent sleeve at the distal end of the guidewire lumen is also useful in other catheter applications. For example, the sleeve 35 can be used in over the wire catheters at the distal end while the portion of the tubular portion 34 in the proximal shaft can be formed of a higher friction material such as HDPE. Over the wire catheters generally include an outer shaft and an inner member. The outer proximal shafts of over the wire catheters are generally formed of polymers such as PEBAX or Nylon, however friction between the proximal shaft and the guide catheter can cause reduced pushability of the catheter. Improvements in pushability have been attempted by "frosting" of the catheter outer surface to reduce friction. According to one embodiment of the present invention a proximal shaft of an over the wire catheter is formed of the high friction material such as HDPE to improve the pushability and trackability of the catheter, while a sleeve formed of a material such as nylon, PEBAX, or other more bondable material is provided in the area of the balloon proximal bond to improve bondability.

In the present application, the use of terms such as "including" is open-ended and is intended to have the same meaning as terms such as "comprising" and not preclude the presence of other structure, material, or acts. Similarly, though the use of terms such as "can" or "may" is intended to be open-ended and to reflect that structure, material, or acts are not necessary, the failure to use such terms is not intended to reflect that structure, material, or acts are essential. To the extent that structure, material, or acts are presently considered to be essential, they are identified as such.

While this invention has been illustrated and described in accordance with a preferred embodiment, it is recognized that variations and changes may be made therein without departing from the invention as set forth in the claims.

What is claimed is:

1. A guidewire lumen for a catheter, comprising a tubular portion and a sleeve disposed over less than an entire length of the tubular portion so that the sleeve is not disposed around at least part of the tubular portion, the tubular portion being formed of a first polymer and the sleeve being formed of a second polymer, the second polymer comprising one or more of a polyamide, a nylon, a polyether block amide, and polyurethane.

2. The guidewire lumen as set forth in claim 1, wherein the first polymer has lower friction passing over a guidewire than the second polymer.

3. The guidewire lumen as set forth in claim 1, wherein the tubular portion is extruded as a single layer tube.

4. The guidewire lumen as set forth in claim 1, wherein the first polymer is HDPE.

5. The guidewire lumen as set forth in claim 1, comprising a tip disposed at a distal end of the tubular portion, a distal end of the tip having a smaller diameter than a proximal end of the tip.

6. The guidewire lumen as set forth in claim 5, wherein the tip is formed of the first polymer.

7. The guidewire lumen as set forth in claim 6, wherein the tip is integral with the tubular portion.

8. The guidewire lumen as set forth in claim 5, wherein the sleeve extends over at least a portion of the tip.

9. The guidewire lumen as set forth in claim 1, comprising a metallic marker band disposed around a portion of the tubular portion, the sleeve being disposed over the marker band and extending from proximate a distal end of the tubular portion to a point proximal of and proximate the marker band.

10. The guidewire lumen as set forth in claim 1, comprising first and second metallic marker bands disposed around first and second portions, respectively, of the tubular portion, the first marker band being disposed closer to a distal end of the tubular portion than the second marker band, the sleeve being disposed over the first and second marker bands and extending from proximate a distal end of the tubular portion to a point proximal of and proximate the second marker band.

11. The guidewire lumen as set forth in claim 1, wherein the sleeve is disposed around at least a proximal end of the tubular portion.

12. The guidewire lumen as set forth in claim 11, wherein the sleeve disposed around the proximal end of the tubular portion is no more than 10 mm in length.

13. The guidewire lumen as set forth in claim 1, wherein the sleeve is disposed around at least a distal end of the tubular portion.

14. The guidewire lumen as set forth in claim 13, wherein the sleeve disposed around the distal end of the tubular portion is no more than 10 mm in length.

15. The guidewire lumen as set forth in claim 1, wherein the sleeve is disposed around at least a distal end and a proximal end of the tubular portion.

16. The guidewire lumen as set forth in claim 15, wherein no sleeve is provided around an intermediate portion of the tubular portion between the sleeve at the proximal end of the tubular portion and the sleeve at the distal end of the tubular portion.

17. The guidewire lumen as set forth in claim 16, wherein the sleeve disposed around the distal end and the sleeve disposed around the proximal end of the tubular portion are each no more than 10 mm in length.

18. The guidewire lumen as set forth in claim 1, wherein the second polymer is adapted to be bonded to a nylon balloon without adhesive.

19. A guidewire lumen for a catheter, comprising a tubular portion formed of a first material and a sleeve formed of a second material disposed around part of the tubular portion so that the sleeve is not disposed around at least part of the tubular portion, and a metallic marker band disposed around and in direct contact with a portion of the tubular portion, the sleeve being disposed over and in direct contact with the marker band and extending from proximate a distal end of the tubular portion to a point proximal of and proximate the marker band.

20. The guidewire lumen for a catheter as set forth in claim 19, wherein a bond strength per unit area between the marker band and the sleeve is greater than a bond strength between the tubular portion and the sleeve.

21. The guidewire lumen for a catheter as set forth in claim 20, wherein a bond strength per unit area between the marker band and the tubular portion is greater than a bond strength between the tubular portion and the sleeve.

22. The guidewire lumen for a catheter as set forth in claim 19, wherein a bond strength per unit area between the marker band and the tubular portion is greater than a bond strength between the tubular portion and the sleeve.

23. The guidewire lumen for a catheter as set forth in claim 19, comprising a first and a second marker band, the first marker band being disposed closer to a distal end of the tubular portion than the second marker band.

24. The guidewire lumen for a catheter as set forth in claim 23, wherein the sleeve is disposed over the first marker band.

25. The guidewire lumen for a catheter as set forth in claim 24, wherein the sleeve is disposed over the second marker band.

26. The guidewire lumen for a catheter as set forth in claim 19, wherein the tubular portion has a smaller diameter proximate the marker band than at a point proximal of the marker band.

27. The guidewire lumen for a catheter as set forth in claim 19, wherein a diameter of the guidewire lumen is substantially uniform over an entire length of the sleeve.

28. A catheter comprising:
a guidewire lumen comprising a tubular portion and proximal and distal sleeves disposed over less than an entire length of the tubular portion so that the sleeve is not disposed around at least part of the tubular portion, the tubular portion being formed of a first material and the sleeves being formed of a second material, and a metallic marker band disposed between the distal sleeve and the tubular portion and in direct contact with the distal sleeve and the tubular portion;
a balloon bonded to the distal sleeve; and
a catheter shaft bonded to the proximal sleeve.

29. The catheter as set forth in claim 28, wherein the balloon is bonded to the distal sleeve without adhesive.

30. The catheter as set forth in claim 28, wherein the catheter shaft is bonded to the proximal sleeve without adhesive.

31. The catheter as set forth in claim 28, wherein a bond strength per unit area between the marker band and the sleeve is greater than a bond strength between the tubular portion and the sleeve.

32. The catheter as set forth in claim 28, wherein a bond strength per unit area between the marker band and the tubular portion is greater than a bond strength between the tubular portion and the sleeve.

33. The catheter as set forth in claim 28, comprising a first and a second marker band, the first marker band being disposed closer to a distal end of the tubular portion than the second marker band.

34. The catheter as set forth in claim 28, wherein the sleeve is disposed over the first marker band.

35. The catheter as set forth in claim 29, wherein the sleeve is disposed over the second marker band.

36. The catheter as set forth in claim 28, wherein the guidewire lumen passes through an opening in a wall of the catheter shaft and the sleeve is bonded to the catheter shaft proximate the opening.

37. The guidewire lumen for a catheter as set forth in claim 19, wherein the sleeve ends proximate the marker band.

* * * * *